United States Patent

Guillonneau et al.

[11] Patent Number: 5,919,791
[45] Date of Patent: Jul. 6, 1999

[54] ELLIPTICINE COMPOUNDS

[75] Inventors: Claude Guillonneau, Clamart; Emile Bisagni, Orsay; Yves Charton, Sceaux; Ghanem Atassi, Saint Cloud; Alain Pierre, Les Alluets le Roi; Stéphane Leonce, Versailles, all of France

[73] Assignee: Adir et Compagnie, Courbevoie, France

[21] Appl. No.: 08/998,922

[22] Filed: Dec. 29, 1997

[30] Foreign Application Priority Data

Dec. 30, 1996 [FR] France .................... 96 16166

[51] Int. Cl.$^6$ .................... A01N 43/42; C07D 471/00
[52] U.S. Cl. .................... 514/285; 546/70
[58] Field of Search .................... 546/70; 514/285

[56] References Cited

FOREIGN PATENT DOCUMENTS 591058  4/1994  European Pat. Off. .

*Primary Examiner*—Mukund J. Shah
*Assistant Examiner*—Tamthom T. Ngo
*Attorney, Agent, or Firm*—The Firm of Gordon W. Hueschen

[57] ABSTRACT

The compounds of formula:

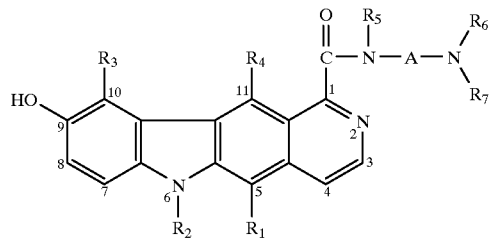

in which: $R_1$, $R_2$, $R_3$, $R_4$, $R_5$, $R_6$, $R_7$ and A are as defined in the description, their optical isomers and N-oxides and addition salts thereof with a pharmaceutically acceptable acid or base, and their use as anti-tumour agents.

12 Claims, No Drawings

ELLIPTICINE COMPOUNDS

The present invention relates to new ellipticine compounds and to pharmaceutical compositions containing them. The compounds of the present invention have a valuable therapeutic use by virtue of their anti-tumour activity.

Some ellipticine compounds are already known for their anti-cancer properties. There may be mentioned by way of example patent specification EP 0 591 058 A1.

The needs of therapeutics demand the constant development of new anti-cancer agents with the aim of obtaining molecules that are both more active and better tolerated.

The present invention relates to ellipticine compounds exhibiting in particular, as compared with the compounds of the prior art, a higher degree of in vitro cytotoxicity, which is indicative of a better therapeutic use.

The present invention relates more particularly to compounds of the general formula I:

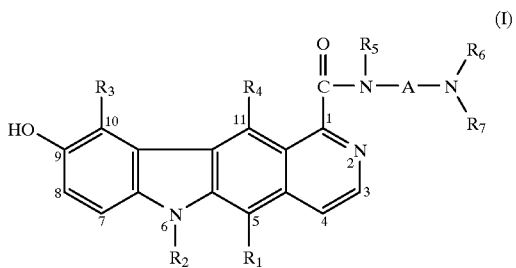

in which:
$R_1$ represents a straight- or branched-chained alkyl radical having from 1 to 6 carbon atoms;
$R_2$, $R_4$ and $R_5$, which may be the same or different, each represents a hydrogen atom or a straight- or branched-chained ($C_1$–$C_6$)alkyl radical;
$R_3$ represents:
a hydrogen atom,
a straight- or branched-chained ($C_1$–$C_6$)alkyl radical which is optionally substituted, on the carbon atom bonded to the tetracycle, by a di($C_1$–$C_6$)alkylamino group, or
a ($C_2$–$C_6$)alkenyl radical;
$R_6$ and $R_7$, which may be the same or different, each represents a hydrogen atom or a ($C_1$–$C_6$)-alkyl radical, in each case in a straight or branched chain, and
$R_6$ and $R_7$ may, together with the nitrogen atom to which they are bonded, form a heterocyclic radical which optionally contains a second hetero atom selected from the atoms nitrogen, oxygen and sulphur, such as, for example, the radicals pyrrolyl, pyrrolinyl, pyrrolidinyl, imidazolyl, imidazolinyl, imidazolidinyl, oxazolyl, oxazolinyl, oxazolidinyl, pyridyl, piperidinyl, morpholinyl, thiomorpholinyl, piperazinyl, pyrazolyl, pyrazolinyl, pyrazolidinyl, pyridazinyl, pyrimidinyl and pyrazinyl, and, furthermore, $R_6$ may be bonded to $R_5$ in order to form together a bridge —$(CH_2)_m$— in which m has the value 2 or 3; and
A represents a saturated linear or branched hydrocarbon chain containing from 1 to 10 carbon atoms, with the proviso, however, that A does not represent a saturated linear hydrocarbon chain having from 1 to 6 carbon atoms when, simultaneously, $R_3$ is hydrogen; as well as their possible optical isomers, N-oxides and pharmaceutically acceptable addition salts with an acid or a base.

The present invention relates also to a process for the preparation of the compounds of formula I, characterised in that
a compound of formula II:

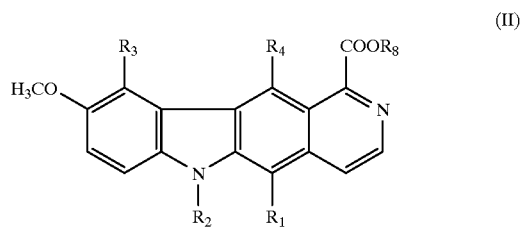

in which:
$R_1$, $R_2$, $R_3$ and $R_4$ are as defined above, and
$R_8$ represents a straight- or branched-chained ($C_1$–$C_6$) alkyl radical,
is reacted
with a hydracid, such as, for example, hydrochloric acid, or with an alkaline agent, such as, for example, sodium hydroxide,
to give a compound of formula III:

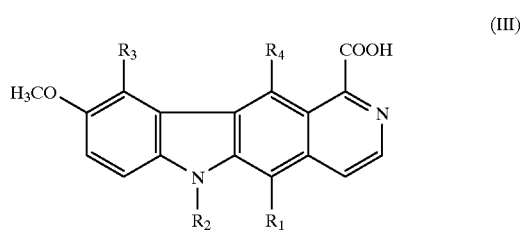

in which $R_1$, $R_2$, $R_3$ and $R_4$ are as defined above, which is reacted with a compound of formula IV:

in which $R_5$, $R_6$, $R_7$ and A are as defined above, to give a compound of formula V:

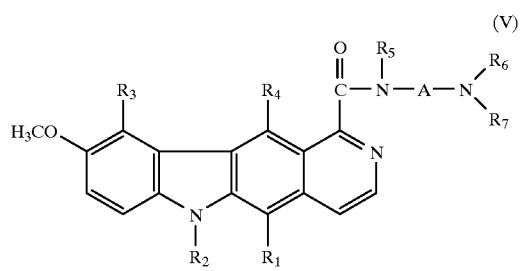

in which $R_1$, $R_2$, $R_3$, $R_4$, $R_5$, $R_6$, $R_7$ and A are as defined above, which is demethylated by means of a Lewis acid, such as, for example, boron tribromide, to yield the corresponding compound of formula I.

The hydrolysis of the compounds II with an alkaline agent such as sodium hydroxide is advantageously effected by carrying out the reaction in a solvent such as aqueous ethanol.

The reaction of the compound of formula III with an amine of formula IV can advantageously be carried out in the presence of a peptide coupling agent such as dicyclohexylcarbodiimide in an aprotic solvent such as dimethylformamide, or in the presence of the cyclic anhydride of 1-propanephosphonic acid (which is a commercially available reagent) in an aprotic solvent such as dimethylformamide, in accordance with the method described by H. WISSMANN and H. J. KLEINER, Angew. Chem. Int. Ed. Engl., 19, 133–134, (1980), or in the presence of benzotriazol-1-yloxytripyrrolidinophosphonium hexafluorophosphate, which is a commercially available product, in accordance with the method described by J. COSTE, D. LE NGUYEN and B. CASTRO, Tetrahedron Letters, 31, 2, 205–208, (1990).

The demethylation of the compounds of formula V can be carried out in a suitable manner in the presence of a Lewis acid such as boron tribromide in an aprotic solvent such as dichloromethane or toluene to yield the compounds of formula I.

Depending on the meanings of the variables $R_1$ to $R_7$, the compounds of formula I can also be prepared in accordance with other variants, all of which form part of the present invention.

Accordingly, the present invention relates also to a process for the preparation of compounds of formula I, characterised in that:

a) a compound of formula IIa:

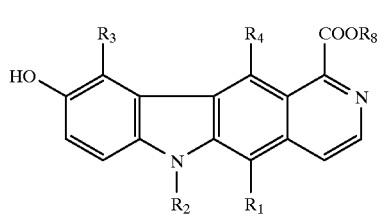

(IIa)

in which $R_1$, $R_2$, $R_3$, $R_4$ and $R_8$ are as defined above, is reacted with a compound of formula IVa:

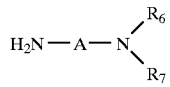

(IVa)

in which $R_6$, $R_7$ and A are as defined above, to give a compound of formula Ia:

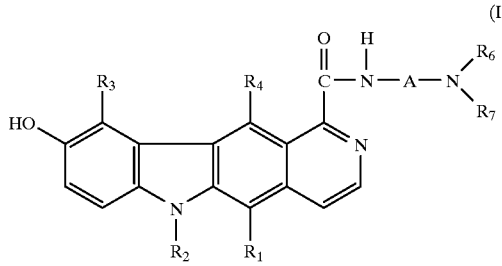

(Ia)

in which $R_1$, $R_2$, $R_3$, $R_4$, $R_6$, $R_7$ and A are as defined above; or b) a compound of formula Ib:

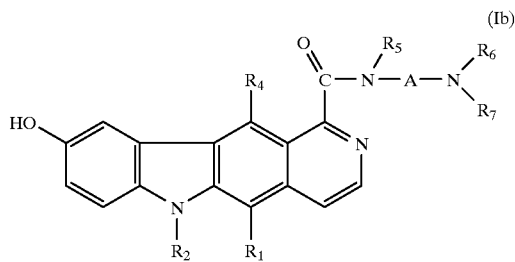

(Ib)

in which $R_1$, $R_2$, $R_4$, $R_5$, $R_6$, $R_7$ and A are as defined above, is reacted either with a compound of formula VI:

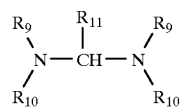

(VI)

in which:
$R_9$ and $R_{10}$, which may be the same or different, each represents a linear or branched $(C_1$–$C_6)$alkyl radical, and
$R_{11}$ represents a radical of the formula: $CnH_{2n+1}$ in which n represents zero or an integer from 1 to 5 inclusive,
or with a compound of formula VII:

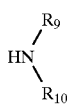

(VII)

in which $R_9$ and $R_{10}$ are as defined above, in the presence of an aldehyde containing from 1 to 6 carbon atoms, to give a compound of formula Ic:

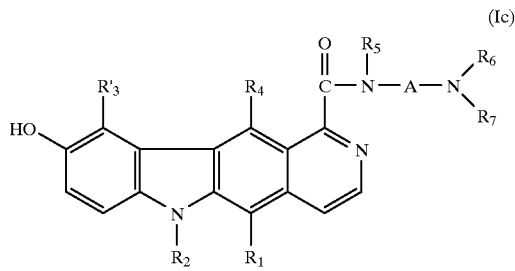

(Ic)

in which:
$R_1$, $R_2$, $R_4$, $R_5$, $R_6$, $R_7$ and A are as defined above, and
$R'_3$ represents: a $(C_1$–$C_6)$alkyl radical which is substituted, on the carbon atom bonded to the tetracycle, by a di$(C_1$–$C_6)$alkylamino group (i.e. a radical:

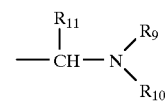

in which $R_9$, $R_{10}$ and $R_{11}$ are as defined above); or
c) a compound of formula Ic defined above is reacted with hydrogen to give a compound of formula Id:

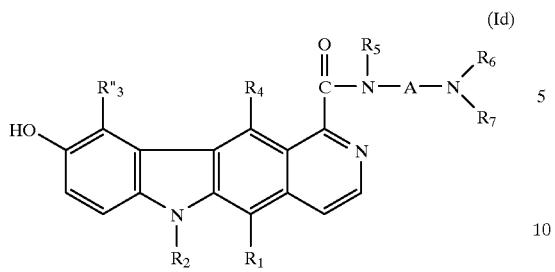

in which:

$R_1$, $R_2$, $R_4$, $R_5$, $R_6$, $R_7$ and A are as defined above, and R"$_3$ represents a ($C_1$–$C_6$)alkyl radical (i.e. the radical —CH$_2$—R$_{11}$ in which R$_{11}$ is as defined above); or d) a compound of formula II'a:

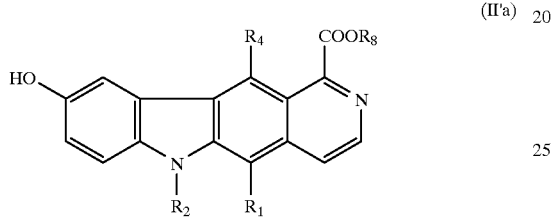

in which $R_1$, $R_2$, $R_4$ and $R_8$ are as defined above, is reacted with a compound of formula VIII:

in which X represents a nucleofugal group such as, for example, a halogen atom or an alkylsulphonate or arylsulphonate group, to give a compound of formula IX:

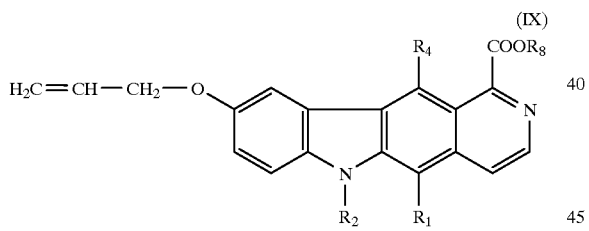

in which $R_1$, $R_2$, $R_4$ and $R_8$ are as defined above, which, by means of thermal rearrangement (allyl transposition), yields the compound of formula IIb:

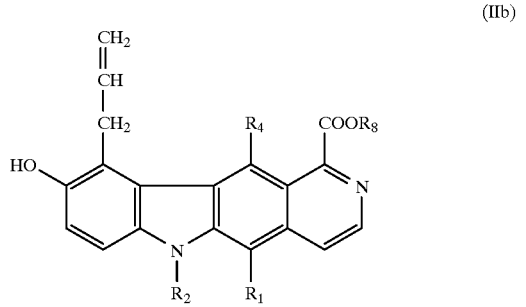

in which $R_1$, $R_2$, $R_4$ and $R_8$ are as defined above, which is reacted with an amine of formula IVa as defined above to give a compound of formula Ie:

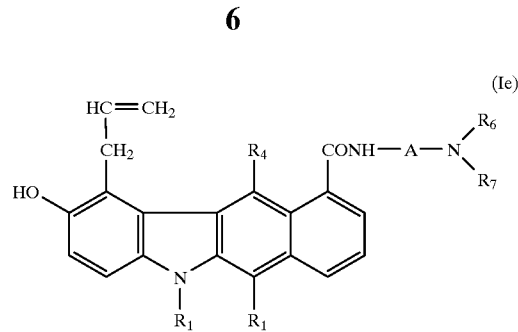

in which $R_1$, $R_2$, $R_4$, $R_6$, $R_7$ and A are as defined above; or e) a compound of formula IIb defined above is hydrogenated to give a compound of formula IIc:

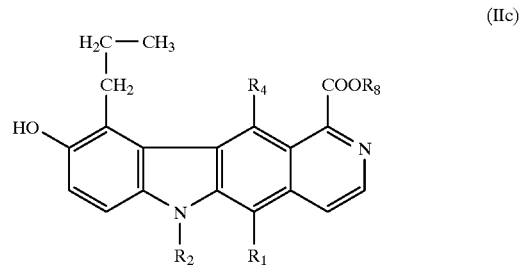

in which $R_1$, $R_2$, $R_4$ and $R_8$ are as defined above, which is reacted with an amine of formula IVa as defined above to give a compound of formula If:

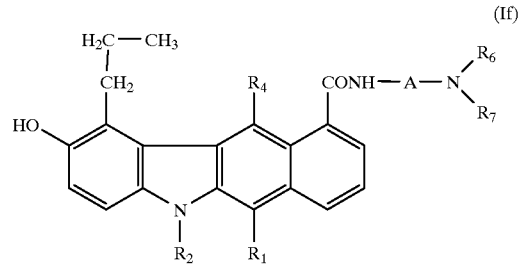

in which $R_1$, $R_2$, $R_4$, $R_6$, $R_7$ and A are as defined above.

The compounds of formulae IIa, IIb and IIc belong to the totality of the compounds of formula II, and the totality of the compounds of formula IVa likewise forms part of the totality of the compounds of formula IV.

The compounds of formulae Ia, Ib, Ic, Id, Ie and If are all included in the totality of the compounds of formula I.

It is especially advantageous to react a compound of formula IIa with a compound of formula IVa, either by using an excess of the compound of formula IVa, or by carrying out the reaction in a suitable solvent such as, for example, a low-boiling alcohol or an aprotic solvent such as tetrahydrofuran or dichloromethane, at a temperature of from 80 to 150° C.

The reaction of a compound of formula Ib with a compound of formula VI can be carried out in an ethereal solvent such as dioxane in the presence of an acid agent such as acetic acid.

The reaction of a compound of formula Ib with a compound of formula VII is carried out in accordance with the method described in Organic Syntheses, Collective Volume IV, p. 626.

The catalytic hydrogenation of the compounds of formula Ic to give the compounds of formula Id can be carried out in the presence of a hydrogenation catalyst such as palladium-on-carbon, palladium-on-barium sulphate or palladium hydroxide-on-carbon, optionally in the presence of an acid, for example in the presence of hydrochloric acid in a low-boiling solvent, or in acetic acid.

The reaction of the compounds of formulae II'a and VIII can be carried out in an aprotic solvent such as dimethylformamide, tetrahydrofuran, acetone or pyridine, in the absence or presence of a hydracid acceptor such as an alkali metal carbonate such as potassium carbonate or of a tertiary amine such as triethylamine or dimethylaminopyridine.

The allyl rearrangement reaction of the compound of formula IX can be carried out in a suitable manner in a high-boiling aprotic solvent such as, for example, diethylamine or 1,2-dichlorobenzene, at the boiling temperature of the solvent used.

The catalytic hydrogenation of the compound of formula IIb to give a compound of formula IIc can be carried out in a low-boiling alcohol such as, for example, ethanol, at a temperature of from 20 to 60°, under a pressure of from $1.10^5$ to $5.10^5$ Pa, in the presence of a hydrogenation catalyst such as, for example, palladium-on-carbon or Raney nickel.

The methods for the preparation of the compounds of formulae II and IIa are described in patent specification EP 0 591 058 A1.

The compounds of formula IV are either commercially available products or compounds that are readily accessible by the conventional methods used in organic chemistry.

The compounds of formula I so prepared can be purified either by low-pressure chromatography (flash chromatography) on silica (AMICON 35–70μ) using as eluant, for example, ethyl acetate or a mixture of dichloromethane and methanol, in the absence or presence of ammonia, or by recrystallisation of the said compounds or of their salts from a customary solvent such as, for example, ethanol, water or dimethylformamide.

The compounds of formula I yield salts with physiologically tolerable acids or bases, which salts are included as such in the present invention.

The compounds of formula I also yield N-oxide compounds, which are also included as such in the present invention.

Some of the compounds of formula I contain one or more asymmetric carbon atoms and, accordingly, yield enantiomers or diastereoisomers, which likewise form part of the present invention.

The compounds of the present invention have pharmacological properties which are particularly valuable, especially an excellent in vitro cytotoxicity and a good anti-tumour activity which, coupled with the fact that the compounds are particularly well tolerated, allows them to be used in the treatment of cancers.

The present invention relates also to pharmaceutical compositions comprising as active ingredient at least one compound of the present invention, in admixture or in association with one or more pharmaceutical excipients or inert, non-toxic carriers.

The pharmaceutical compositions are generally in dosage unit form suitable for administration orally, rectally or parenterally, and especially in the form of tablets, dragées, gelatin capsules, suppositories and injectable or drinkable solutions.

The dosage varies according to the age and weight of the patient, the mode of administration, the nature of the therapeutic indication and any associated treatments and ranges from 0.1 to 400 mg per day administered in one or more doses.

The Examples which follow illustrate the present invention, melting points being determined using a Kofler hot plate (K) or by means of a capillary tube (cap.).

EXAMPLE 1

1-[(3-Dimethylamino-2,2-dimethylpropyl) aminocarbonyl]-5,6-dimethyl-9-hydroxy-6H-pyrido[4,3-b] carbazole dihydrochloride

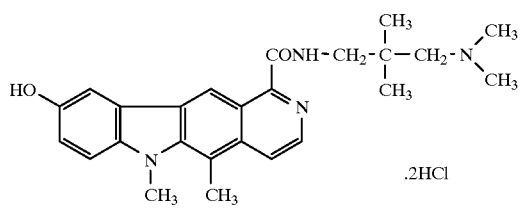

8 g of 1-(methoxycarbonyl)-5,6-dimethyl-9-hydroxy-6H-pyrido[4,3-b]carbazole in 120 ml of N,N,2,2-tetramethyl-1,3-propanediamine are stirred at 130° C. for 20 hours. Concentration to dryness is carried out under a vane pump vacuum and the residue (made into a paste with 40 g of silica) is chromatographed on 720 g of silica using a dichloromethane/ethanol mixture (90/10) as eluant. The pure fractions are concentrated to dryness and the residue is suspended in 60 ml of ethanol. 20 ml of ethanolic hydrogen chloride are added, and dissolution and then crystallisation are observed. The mixture is suction-filtered and dried at 50° C. under 66.6 Pa. 1 g of the desired product is obtained, m.p. (cap): 275–280° C. Yield: 10%.

EXAMPLE 2

1-[(2-Dimethylaminoethyl)aminocarbonyl]-5,6-dimethyl-9-hydroxy-10-dimethylaminomethyl-6H-pyrido [4,3-b]carbazole trihydrochloride

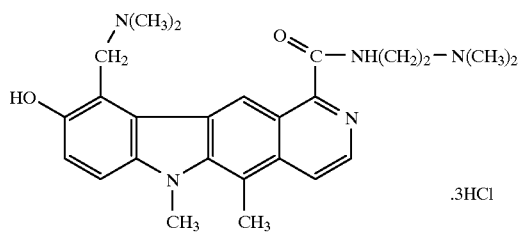

0.9 g of 1-[(2-dimethylaminoethylaminocarbonyl)-5,6-dimethyl-9-hydroxy-6H-pyrido[4,3-b]-carbazole, 3.25 g of N,N,N',N'-tetramethyldiaminomethane, 0.3 ml of acetic acid and 72 ml of dioxane are refluxed for 30 minutes. Concentration to dryness is carried out. The residue is taken up in water, neutralised using concentrated ammonia and extracted with dichloromethane with the addition of ethanol until dissolution is complete. The organic phase is dried over magnesium sulphate and then evaporated to dryness. The residue is stirred in diethyl ether, suction-filtered and taken up in ethanol. Ethanolic hydrogen chloride is added to pH<3. The insoluble material is suction-filtered and then washed with ethanol and with ether and dried at 50° C. in vacuo. 1.04 g of the desired product are obtained, m.p. (K):>250° C. Yield: 80%.

EXAMPLE 3

1-[(2-Dimethylaminoethyl)aminocarbonyl]-5,6,10-trimethyl-9-hydroxy-6H-pyrido[4,3-b]-carbazole

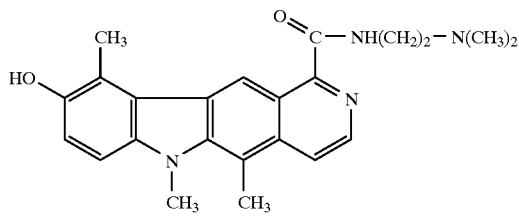

2.6 g of 1-[(2-dimethylaminoethyl)aminocarbonyl]-5,6-dimethyl-9-hydroxy-10-dimethylaminomethyl-6H-pyrido[4,3-b]carbazole are hydrogenated in 1.2 litres of ethanol in the presence of 2.2 g of 10% palladium-on-carbon at 30° C. for 4 hours (after which time only a minor amount of the starting material remains) under a hydrogen pressure of $1.10^5$ Pa. Filtration is carried out and the precipitate is washed with a dichloromethane/ethanol mixture. The combined filtrates are concentrated to dryness. The residue is chromatographed on silica using as eluant first a dichloromethane/ethanol mixture and then a dichloromethane/ethanol/triethylamine mixture. 0.23 g of the desired product is obtained, m.p. (K): 170° C. Yield: 10%.

EXAMPLE 4

1-[(2-Dimethylaminoethyl)aminocarbonyl]-5,6-dimethyl-9-hydroxy-10-allyl-6H-pyrido[4,3-b]carbazole

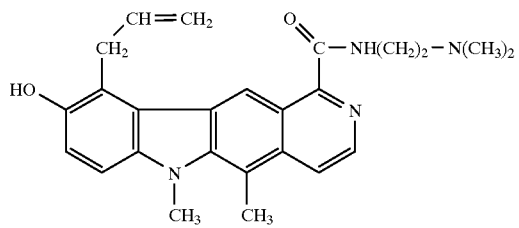

2 g of 1-ethoxycarbonyl-5,6-dimethyl-9-allyloxy-6H-pyrido[4,3-b]carbazole are dissolved in 80 ml of 1,2-dichlorobenzene, and the solution is refluxed for 10 hours. The mixture is cooled and precipitation is observed. The precipitate is suction-filtered and chromatographed on silica using as eluant first dichloromethane and then a dichloromethane/ethanol mixture. 1.27 g of 1-ethoxycarbonyl-5,6-dimethyl-9-hydroxy-10-allyl-6H-pyrido[4,3-b]carbazole are obtained.

That compound was converted into 1-[(2-dimethylaminoethyl)aminocarbonyl]-5,6-dimethyl-9-hydroxy-10-allyl-6H-pyrido[4,3-b]carbazole using the method described in Example 1 with a yield of 75%, m.p. (K): 222° C.

EXAMPLE 5

1-[(2-Dimethylaminoethyl)aminocarbonyl]-5,6-dimethyl-9-hydroxy-10-propyl-6H-pyrido-[4,3-b]carbazole

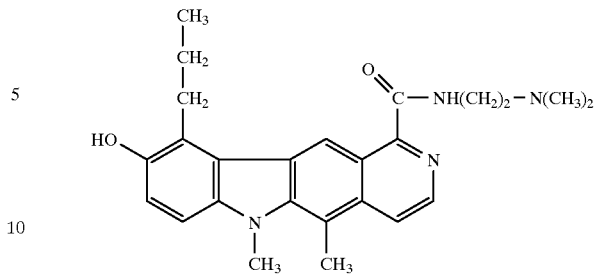

0.7 g of 1-ethoxycarbonyl-5,6-dimethyl-9-hydroxy-10-allyl-6H-pyrido[4,3-b]carbazole is hydrogenated in 200 ml of ethanol in the presence of 0.3 g of 10% palladium-on-carbon at 40° C. under a hydrogen pressure of $1.10^5$ Pa for 30 minutes. Filtration is carried out, the catalyst is washed with ethanol and the combined filtrates are concentrated to dryness. The residue is chromatographed on silica using as eluant first dichloromethane and then a dichloromethane/ethanol mixture (98/2). 0.362 g of 1-ethoxycarbonyl-5,6-dimethyl-9-hydroxy-10-propyl-6H-pyrido[4,3-b]carbazole is obtained. Yield: 51%.

That compound is converted into 1-[(2-dimethylaminoethyl)aminocarbonyl]-5,6-dimethyl-9-hydroxy-10-propyl-6H-pyrido[4,3-b]carbazole using the method described in Example 1 in a yield of 69%, m.p. (K): 211° C.

EXAMPLE 6

PHARMACOLOGICAL STUDY

Cytotoxicity Study

Four cell lines were used:

1 murine leukaemia, L 1210, 1 human pulmonary carcinoma, A 549, 1 human epidermoid carcinoma, KB-3-1, the corresponding resistant line, KB-A1, whose multidrug resistance has been induced by adriamycin (ADR).

The cells are cultured in RPMI 1640 complete culture medium containing 10% foetal calf serum, 2 mM glutamine, 50 units/ml of penicillin, 50 µg/ml of streptomycin and 10 mM Hepes, pH=7.4.

The cells are distributed on microplates and exposed to the cytotoxic compounds. The cells are then incubated for 2 days (L 1210) and 4 days (A 549, KB-3-1, KB-A1). The number of viable cells is then quantified by means of a calorimetric assay, the Microculture Tetrazolium Assay (Carmichael J., DeGraff W. G., Gazdar A. F., Minna J. D. and Mitchell J. R., Evaluation of a tetrazolium-based semi-automated colorimetric assay: assessment of chemosensitivity testing, Cancer Res., 47, 936–942, 1987).

The results are expressed as $IC_{50}$, the concentration of cytotoxic agent which inhibits the proliferation of the treated cells by 50%. The results obtained on the lines used are shown in the Table below.

By way of example, the results obtained with the compound of Example 3, which is particularly representative of the invention, and with adriamycin (ADR) as reference product are shown below.

| Test compounds | IC$_{50}$ (nM) | | | |
| --- | --- | --- | --- | --- |
| | L 1210 | A 549 | KB-3-1 | KB-A1 |
| Example 3 | 3.5 | 6.5 | 6.3 | 329.1 |
| ADR | 24.3 | 39.8 | 18.1 | 6746 |

The cytotoxicity of the compound of Example 3 is greater than that of adriamycin on the four lines tested. That compound and all the other compounds of the present invention can therefore be used successfully against tumours that are resistant to adriamycin and have the phenotype of multidrug resistance.

We claim:

1. A compound selected from the group consisting of those of formula I:

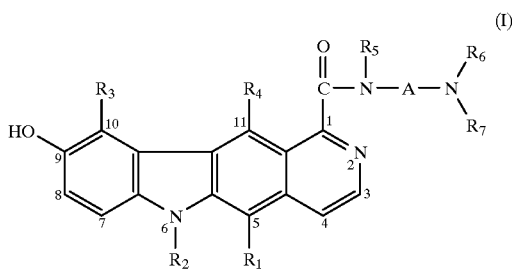

(I)

in which:

$R_1$ is selected from the group consisting of: straight-chained ($C_1$–$C_6$) alkyl and branched-chain ($C_2$–$C_6$) alkyl, $R_2$, $R_4$ and $R_5$, which are the same or different, are each selected from the group consisting of hydrogen and straight-chained ($C_1$–$C_6$)alkyl and branched-chained ($C_2$–$C_6$) alkyl;

$R_3$ is selected from the group consisting of:
  hydrogen,
  unsubstituted straight-chained ($C_1$–$C_6$) alkyl and branched-chained ($C_2$–$C_6$) alkyl and
  straight-chained ($C_1$–$C_6$)alkyl and branched-chained ($C_2$–$C_6$) alkyl which are substituted, on the carbon atom bonded to the tetracycle, by di($C_1$–$C_6$) alkylamino, and
  ($C_2$–$C_6$)alkenyl;

$R_6$ and $R_7$, which are the same or different, are each selected from the group consisting of: hydrogen and straight-chain ($C_1$–$C_6$) alkyl and branch-chained ($C_2$–$C_6$) alkyl, or $R_6$ and $R_7$, together with the nitrogen atom to which they are bonded, form a heterocyclic group which optionally contains a second hetero atom selected from nitrogen, oxygen, and sulphur, and, furthermore, $R_6$ maybe bonded to $R_5$ in order to form together a bridge —(CH$_2$)$_m$— in which m is an integer selected from the goup consisting of 2 and 3;

A is selected from the group consisting of saturated linear ($C_1$–$C_{10}$) and branched ($C_2$–$C_{10}$) hydrocarbon chains, with the proviso, however, that A does not represent a saturated linear ($C_1$–$C_6$) hydrocarbon chain when, simultaneously, $R_3$ is hydrogen;

their optical isomers and their N-oxides, and addition salts thereof with pharmaceutically-acceptable acids or bases.

2. A compound of claim 1 which is 1-[(2-dimethylaminoethyl)aminocarbonyl]-5,6,10-trimethyl-9-hydroxy-6H-pyrido[4,3-b]carbazole.

3. A method for treating a living animal body afflicted with cancer, comprising the step of administering to said living animal body an amount of a compound of claim 1 which is suitable for alleviation of said cancer.

4. A pharmaceutical composition, useful as an anti-tumour agent, comprising as active ingredient an effective anti-tumor amount of a compound according to claim 1 together with one or more pharmaceutically-acceptable excipients or vehicles.

5. A method for treating a living animal body afflicted with a cancer, comprising the step of administering to said living animal body an amount of a compound of claim 2 which is suitable for alleviation of said cancer.

6. A pharmaceutical composition, useful as an anti-tumour agent, comprising as active ingredient an effective anti-tumour amount of a compound according to claim 2 together with one or more pharmaceutically-acceptable excipients or vehicles.

7. A compound of claim 1 which is selected from the group consisting of 1-[(3-Dimethylamino-2,2-dimethylpropyl)aminocarbonyl]-5,6-dimethyl-9-hydroxy-6H-pyrido[4,3-b]carbazole and a pharmaceutically-acceptable acid addition salt thereof.

8. A compound of claim 1 which is selected from the group consisting of 1-[(3-Dimethylamino-2,2-dimethylpropyl)aminocarbonyl]-5,6-dimethyl-9-hydroxy-6H-pyrido[4,3-b]carbazole and its dihydrochloride.

9. A compound of claim 1 which is selected from the group consisting of 1-[(2-Dimethylaminoethyl)aminocarbonyl]-5,6-dimethyl-9-hydroxy-10-dimethylaminomethyl-6H-pyrido[4,3-b]carbazole and a pharmaceutically-acceptable acid addition salt thereof.

10. A compound of claim 1 which is selected from the group consisting of 1-[(2-Dimethylaminoethyl)aminocarbonyl]-5,6-dimethyl-9-hydroxy-10-dimethylaminomethyl-6H-pyrido[4,3-b]carbazole and its trihydrochloride.

11. A compound of claim 1 which is selected from the group consisting of 1-[(2-Dimethylaminoethyl)-aminocarbonyl]-5,6-dimethyl-9-hydroxy-10-allyl-6H-pyrido[4,3-b]carbazole and a pharmaceutically-acceptable acid addition salt thereof.

12. A compound of claim 1 which is selected from the group consisting of 1-[(2-Dimethylaminoethyl)-aminocarbonyl]-5,6-dimethyl-9-hydroxy-10-propyl-6H-pyrido[4,3-b]carbazole and a pharmaceutically-acceptable acid addition salt thereof.

* * * * *

UNITED STATES PATENT AND TRADEMARK OFFICE
CERTIFICATE OF CORRECTION

PATENT NO. : 5,919,791
DATED : July 6, 1999
INVENTOR(S) : C. Guillonneau, E. Bisagni, Y. Charton, G. Atassi, A. Piere, S. Leonce It is certified that error appears in the above-indentified patent and that said Letters Patent is hereby corrected as shown below:

Column 11, line 33: "branched-chain" should read -- branched-chained --.

Column 11, line 56: "maybe" should read -- may be --.

Column 12, line 12: "with cancer" should read -- with a cancer --.

Signed and Sealed this

Twenty-third Day of November, 1999

Q. TODD DICKINSON

Attest:

Attesting Officer

Acting Commissioner of Patents and Trademarks